United States Patent
Skiffington et al.

(10) Patent No.: US 10,495,563 B1
(45) Date of Patent: Dec. 3, 2019

(54) PLATE READER OBSERVATION METHODS AND OPERATION

(71) Applicant: Charm Sciences, Inc., Lawrence, MA (US)

(72) Inventors: Richard T. Skiffington, North Reading, MA (US); Robert S. Salter, Reading, MA (US); Robert J. Markovsky, Brentwood, NH (US); Stanley E. Charm, Boston, MA (US)

(73) Assignee: Charm Sciences, Inc., Lawrence, MA (US)

( * ) Notice: Subject to any disclaimer, the term of this patent is extended or adjusted under 35 U.S.C. 154(b) by 0 days.

(21) Appl. No.: 15/581,470

(22) Filed: Apr. 28, 2017

Related U.S. Application Data

(60) Provisional application No. 62/328,674, filed on Apr. 28, 2016, provisional application No. 62/330,408, filed on May 2, 2016.

(51) Int. Cl.
| | | |
|---|---|---|
| G06K 9/00 | (2006.01) | |
| G01N 15/14 | (2006.01) | |
| C12Q 1/02 | (2006.01) | |
| G06T 7/00 | (2017.01) | |
| G06T 7/11 | (2017.01) | |
| G06T 5/20 | (2006.01) | |
| G08B 21/18 | (2006.01) | |
| G06T 5/40 | (2006.01) | |
| G01N 15/10 | (2006.01) | |
| G01N 15/00 | (2006.01) | |

(52) U.S. Cl.
CPC .......... *G01N 15/1463* (2013.01); *C12Q 1/02* (2013.01); *G06T 5/20* (2013.01); *G06T 5/40* (2013.01); *G06T 7/0016* (2013.01); *G06T 7/11* (2017.01); *G08B 21/182* (2013.01); *G01N 2015/0065* (2013.01); *G01N 2015/1006* (2013.01); *G01N 2015/1486* (2013.01); *G06T 2207/30242* (2013.01)

(58) Field of Classification Search
CPC combination set(s) only.
See application file for complete search history.

(56) References Cited

U.S. PATENT DOCUMENTS

| | | | |
|---|---|---|---|
| 5,443,963 A | 8/1995 | Lund | 435/34 |
| RE35,286 E | 6/1996 | Nelson et al. | 435/243 |
| 5,545,535 A | 8/1996 | Roth et al. | 435/34 |
| 5,585,273 A | 12/1996 | Lawrence et al. | 435/288.7 |
| 5,723,308 A | 3/1998 | Mach et al. | 435/34 |
| 5,837,482 A | 11/1998 | Mach et al. | 435/34 |
| 5,854,056 A | 12/1998 | Dschida | 435/254.1 |
| 5,869,321 A | 2/1999 | Franklin | 435/253.6 |
| 5,958,675 A | 9/1999 | Wicks et al. | 435/5 |
| 6,051,388 A | 4/2000 | Bodenhamer | 435/7.32 |
| 6,103,528 A | 8/2000 | An et al. | 435/395 |
| 6,174,699 B1 | 1/2001 | Wickert et al. | 435/34 |
| 6,218,184 B1 | 4/2001 | Hasegawa et al. | 435/431 |

(Continued)

*Primary Examiner* — Alex Kok S Liew
(74) *Attorney, Agent, or Firm* — MacCord Mason PLLC

(57) ABSTRACT

Reader observation and monitoring of the imaging of biological development is shown and described. In one embodiment, a method for monitoring biological growth includes identifying an alert from comparing a background value identified on a plate to a non-background value identified on a plate. In particular examples, a pre-filter, threshold, and histogram analysis identifies an alert count.

20 Claims, 15 Drawing Sheets

(56) References Cited

U.S. PATENT DOCUMENTS

| | | | |
|---|---|---|---|
| 6,243,486 B1 | 6/2001 | Weiss | 382/133 |
| 6,251,624 B1 | 6/2001 | Matsumura et al. | 435/34 |
| 6,372,485 B1 | 4/2002 | Clark et al. | 435/288.7 |
| 6,381,353 B1 | 4/2002 | Weiss | 382/133 |
| 6,391,578 B2 | 5/2002 | Williams et al. | 435/39 |
| 6,391,626 B1 | 5/2002 | Adams et al. | 435/287.9 |
| 6,395,504 B1 | 5/2002 | Trudil | 435/29 |
| 6,492,133 B1 | 12/2002 | Wickert et al. | 435/34 |
| 6,548,263 B1 | 4/2003 | Kapur et al. | 435/7.2 |
| 6,596,532 B1 | 7/2003 | Hyman et al. | 435/287.8 |
| 6,630,457 B1 | 10/2003 | Aeschlimann et al. | 514/54 |
| 6,632,661 B2 | 10/2003 | Wickert | 435/305.4 |
| 6,638,755 B2 | 10/2003 | Mizuochi et al. | 435/253.6 |
| 6,696,264 B2 | 2/2004 | Bodenhamer et al. | 435/7.9 |
| 6,710,879 B1 | 3/2004 | Hansen et al. | 356/436 |
| 6,711,283 B1 | 4/2004 | Soenksen | 382/133 |
| 6,716,588 B2 | 4/2004 | Sammak et al. | 435/7.2 |
| 6,756,225 B2 | 6/2004 | Bedingham et al. | 435/305.1 |
| 6,770,454 B2 | 8/2004 | Reilly et al. | 435/34 |
| 6,900,028 B2 | 5/2005 | Wickert et al. | 435/29 |
| 6,919,960 B2 | 7/2005 | Hansen et al. | 356/436 |
| 6,961,476 B2 | 11/2005 | Atkinson | 382/272 |
| 7,057,721 B2 | 6/2006 | Gardiner, Jr. et al. | 356/301 |
| 7,068,365 B2 | 6/2006 | Hansen et al. | 356/246 |
| 7,087,401 B2 | 8/2006 | Sandberg et al. | 435/34 |
| 7,141,387 B2 | 11/2006 | Ushiyama | 435/34 |
| 7,183,073 B2 | 2/2007 | Hyman et al. | 435/29 |
| 7,298,886 B2 | 11/2007 | Plumb et al. | 382/133 |
| 7,319,031 B2 | 1/2008 | Vent et al. | 435/286.2 |
| 7,351,574 B2 | 4/2008 | Vent | 435/286.2 |
| 7,358,082 B2 | 4/2008 | Tsuzuki et al. | 435/293.1 |
| 7,415,144 B2 | 8/2008 | Imaizumi et al. | 382/128 |
| 7,496,225 B2 | 2/2009 | Graessle et al. | 382/133 |
| 7,582,415 B2 | 9/2009 | Straus | 435/4 |
| 7,611,862 B2 | 11/2009 | Ponce | 435/34 |
| 7,618,794 B2 | 11/2009 | McKeon | 435/30 |
| 7,727,513 B2 | 6/2010 | MacDonald et al. | 424/9.6 |
| 7,738,689 B2 | 6/2010 | Plumb et al. | 382/133 |
| 7,865,008 B2 | 1/2011 | Graessle et al. | 382/133 |
| 7,901,933 B2 | 3/2011 | Green et al. | 435/287.9 |
| 7,957,575 B2 | 6/2011 | Plumb et al. | 382/133 |
| 7,993,905 B2 | 8/2011 | Singhvi et al. | 135/283.1 |
| 8,021,848 B2 | 9/2011 | Straus | 435/7.1 |
| 8,081,312 B2 | 12/2011 | Hansen et al. | 356/436 |
| 8,094,916 B2 | 1/2012 | Graessle et al. | 382/133 |
| 8,125,643 B2 | 2/2012 | Hansen et al. | 356/436 |
| 8,159,675 B2 | 4/2012 | Kiyota | 356/416 |
| 8,206,983 B2 | 6/2012 | Jayakumar et al. | 435/420 |
| 8,252,549 B2 | 8/2012 | Rao et al. | 435/34 |
| 8,252,590 B2 | 8/2012 | Jorquera Nieto et al. | 435/404 |
| 8,260,026 B2 | 9/2012 | Plumb et al. | 382/133 |
| 8,363,221 B2 | 1/2013 | Hansen et al. | 356/436 |
| 8,417,013 B2 | 4/2013 | Bolea et al. | 382/133 |
| 8,417,014 B2 | 4/2013 | Bolea | 382/133 |
| 8,432,550 B2 | 4/2013 | Hansen et al. | 356/436 |
| 8,447,092 B2 | 5/2013 | Kii et al. | 382/133 |
| 8,588,505 B2 | 11/2013 | Bolea | 382/133 |
| 8,741,595 B2 | 6/2014 | Kshirsagar | 435/54 |
| 8,753,834 B2 | 6/2014 | Miller et al. | 435/34 |
| 8,759,080 B2 | 6/2014 | Graessle et al. | 435/287.3 |
| 8,828,653 B2 | 9/2014 | Zook et al. | 435/4 |
| 8,828,682 B2 | 9/2014 | Mach et al. | 435/39 |
| 8,828,725 B2 | 9/2014 | Fan et al. | 435/404 |
| 8,831,313 B2 | 9/2014 | Li et al. | 382/128 |
| 8,835,173 B2 | 9/2014 | Hattori et al. | 435/404 |
| 8,846,334 B2 | 9/2014 | Young et al. | 435/34 |
| 8,846,335 B2 | 9/2014 | Moeller et al. | 435/34 |
| 8,871,514 B2 | 10/2014 | Hartle et al. | 435/430 |
| 8,921,067 B2 | 12/2014 | Chandrapati et al. | 435/34 |
| 9,442,282 B2 | 9/2016 | Kuroda et al. | 348/79 |
| 2003/0123749 A1* | 7/2003 | Cheng | G06T 5/30 382/275 |
| 2005/0026135 A1 | 3/2005 | Gazenko | 435/4 |
| 2005/0053266 A1* | 3/2005 | Plumb | G06K 9/00127 382/128 |
| 2005/0239200 A1 | 10/2005 | Beckwith et al. | 435/299.1 |
| 2005/0276456 A1 | 12/2005 | Yamato et al. | 382/128 |
| 2010/0291663 A1 | 11/2010 | Koshiba | 435/286.1 |
| 2011/0013820 A1* | 1/2011 | Reed | B82Y 35/00 382/133 |
| 2011/0102582 A1* | 5/2011 | Graessle | G01N 15/1475 348/135 |
| 2011/0153220 A1 | 6/2011 | Bolea et al. | 702/19 |
| 2012/0121543 A1 | 5/2012 | Teather et al. | 424/93.2 |
| 2012/0134571 A1 | 5/2012 | Ito et al. | 382/133 |
| 2013/0084624 A1 | 4/2013 | Waku et al. | 435/253.6 |
| 2014/0057342 A1 | 2/2014 | Uozumi | 435/288.7 |

* cited by examiner

PLATE READER OBSERVATION METHODS AND OPERATION

This application claims the benefit of U.S. provisional application No. 62/328,674, filed Apr. 28, 2016, and U.S. provisional application No. 62/330,408, filed May 2, 2016, both of which are incorporated herein by reference in their entireties.

FIELD OF THE TECHNOLOGY

The present disclosure relates generally to biological testing, and more particularly to improved observation and monitoring of test development.

BACKGROUND

It is desirable to provide rapid, effective detection and identification of various and numerous microorganisms in test samples, such as samples of water, food, such as milk, and body fluids. Microorganisms of interest include all aerobic bacteria and specific bacterial groups, such as coliforms. Other microorganisms of interest include a variety of yeast, molds, and the like.

Classical methods for culturing various microorganisms for detection and identification thereof include the spread plate method, the pour plate method and the liquid medium method. In these traditional methods and devices, biological testing is used to identify and quantify the presence of biological matter in samples. Often, these results are used to diagnose biological concerns and begin remedial measures. Particularly in the food industry, where testing is very cost-sensitive, early and accurate diagnosis is desired. In addition, reducing human error is desired, particularly where users might not be laboratory-trained technicians. Tests used must, therefore, be user-friendly and inexpensive without sacrificing accuracy.

Therefore, Applicants desire systems and methods for monitoring of the imaging of biological development, without the drawbacks presented by traditional arrangements.

SUMMARY

In accordance with the present disclosure, methods of operating improved plate readers are provided to monitor object imaging development. This disclosure provides improved operations and methods that are convenient, efficient, and safe for the user, particularly when used to identify statistically unexpected results, alert counts, and the like.

In one embodiment of the disclosure, a method for monitoring imaging of objects on a growth plate comprises imaging the growth plate with an imaging device positioned above the growth plate to generate at least one image; counting biological growth, when present, on the image; and identifying alert counts on the image by comparing a background brightness value identified on a plate to a non-background brightness value identified on a plate.

In some examples, the method includes triggering an alert message. The alert message may be a too numerous to count (TNTC) interpretation. The method may include alerting a user to perform a manual determination. Further, the method may include overriding the alert message. For instance, overriding may include identifying a plurality of larger size particulates and grouping them as a spreader colony, proper biological growth or other development, or the like.

In particular examples, the method includes pre-filtering the image, for instance a binary histogram for colony/matrix. Further, the method may include thresholding the image. In addition, the method may include performing a histogram analysis of the image. For instance, determining a percentage of the image corresponding with a blank image and determining a percentage of the plate image identified as non-background, including object image(s).

In another embodiment of the disclosure, a method of identifying alert counts on an image of a growth plate comprises pre-filtering the image; thresholding the image; performing a histogram analysis of the image, and wherein identifying the alert counts includes comparing at least one background value identified on a plate to at least one non-background value identified on a plate, including object image(s).

In some examples, the background and object non-background values comprise object size. The method may include generating an alert message, including any alert or error message shown and described herein. For instance, the alert message may be a TNTC error message, while other examples include additional overgrown plate alerts and the like. Further, the method may include overriding the alert message. For instance, overriding may include identifying a spreader colony interpretation, expected biological growth arrangement or other development, or the like.

In particular examples, the background and non-background values comprise a brightness value, such as a gray scale brightness color value, de-speckled adjusted binary histogram analysis, or similar valuation evaluation. The method may include generating an alert message. For instance, the alert message may be a TNTC interpretation, while other examples include additional overgrown plate alerts and the like. Further, the method may include overriding the alert. For instance, overriding may include identifying at least one spreader colony, expected biological growth arrangement or other development, or the like.

In particular examples, the background and non-background values comprise a combination of object size and brightness values, including any of the steps and operations shown and described herein.

Another embodiment of the disclosure includes a method for monitoring objects, when present, on a growth plate, comprising receiving at least one growth plate in a tray holder and transporting the growth plate into a focal alignment with an imaging device; selecting a plate type input from at least a first plate type selection and a second plate type selection, for instance a blank plate or the like background; imaging the growth plate with an imaging device positioned above the tray holder to generate an image; counting objects on said second plate type image; and identifying alert counts by comparing a background value to a non-background value by pre-filtering the image, thresholding the image, and performing a histogram analysis of the image.

In some examples, the method includes triggering an alert message, for instance a TNTC interpretation, while other examples include additional overgrown plate errors and the like. Further, the operation may include overriding the suggested interpretation by identifying a plurality of larger size particulates and grouping them as a spreader colony. Further, the method may include alerting a user to perform a manual determination.

Yet another embodiment includes selecting a plate type between at least two plate type options on a user interface. Selecting the plate type occurs prior to activating a plate imaging.

In certain examples, a plate type selection may include an *E-coli* and coliform plate selection, an aerobic bacteria plate selection, a yeast and mold plate selection, a heterotrophic plate selection, a combination thereof, and the like. In certain operations, selecting the *E-coli* and coliform plate selection initiates a monitoring sequence detecting and enumerating coliform bacteria on the growth plate. The operation may include loading average and background images based on the *E-coli* and coliform plate selection. Further, the operation may include cropping an average image to yield active plate portions, cropping background images, and dividing the average image by the background image to yield a background-subtracted image. In yet other examples, selecting aerobic bacteria plate selection initiates a monitoring sequence detecting and enumerating aerobic bacteria on the growth plate. The method may include cropping an average image to yield active plate portions, cropping background images, and dividing the average image by the background image to yield a background-subtracted image.

In further embodiments, an assembly for monitoring biological growth comprises a reader having a plate imaging unit with an imaging device and a tray holder, and wherein the tray holder receives the growth plate externally from the plate imaging unit and transports the growth plate into the plate imaging unit to a focal alignment with the imaging device; a processor in electrical communication with the reader and having an image processing engine adapted to perform colony counting to monitor the biological growth, when present; a user interface in electrical communication with the reader and to display a result display; and at least one growth plate having a recessed well with a sunken wall protruding below an upper face.

In some examples, the assembly includes an illumination system having an upper illumination dome having a plurality of light emitting diodes and a lower backlight diffuser. The reader, processor, and user interface may be aligned substantially adjacent to one another on a bench top. The reader, processor, and user interface may be integral with one another. The reader may have a base plate including a backstop and an opposing open portion. The tray holder may include a sunken support frame adapted to receive and retain an inverted plate in a semi-fixed position. The tray holder may include a stationary end rotatably affixed to the base plate, and a traversing end adapted to allow entry and exit into the base plate along a single radial axis. Further, the growth plate may include a pair of opposing proximate extensions adjacent the recessed well and extending above the upper face, and a distal raised platform adjacent the recessed well and extending above the upper face.

In another embodiment, a device for monitoring biological growth, when present, on a growth plate comprises a reader having a housing with a plurality of openings, a plate imaging unit with an illumination system, an imaging device positionable about the illumination system, and a tray holder, and wherein the tray holder receives a growth plate externally through at least one opening and transports the growth plate into the plate imaging unit to a focal alignment with the imaging device; and a processor in electrical communication with the imaging device and having an image processing engine adapted to perform colony counting to monitor the biological growth, when present.

In particular examples, the housing has a top imaging aperture. Typically, the imaging device is aligned with the top imaging aperture. Further, the imaging device may be spaced offset from the top imaging aperture.

In some examples, an alignment bracket is positioning the illumination system about the imaging unit. For instance, the alignment bracket may include a lower fitting affixed to the illumination system and an upper fitting affixed to the imaging unit. The lower fitting and upper fitting may be positioned together with at least one adjustment. In certain examples, the at least one adjustment includes an off-axis adjustment.

In certain examples, a user interface is in electrical communication with the processor. Further, the tray holder may receive and retain a growth plate having a recessed well with a sunken wall protruding below an upper face, a pair of opposing proximate extensions adjacent the recessed well and extending above the upper face, and a distal raised platform adjacent the recessed well and extending above the upper face. The tray holder may include a stationary end rotatably affixed to the baseplate. The tray holder may include a sunken support frame adapted to receive and retain the plate in a semi-fixed position. The tray holder may have distal platform aperture, a well aperture, and pair of opposing proximate apertures are adapted to receive and mate with a corresponding inverted growth plate's recessed well, pair of opposing proximate extensions, and the distal raised platform. In addition, the device may include a baseplate includes at least one mechanical backstop defining an alignment cradle to align the tray holder in a processing position.

Yet another embodiment of the disclosure is a reader having a housing with a plurality of openings; a reader secured within the housing and having a plate imaging unit with an illumination system, an imaging device positionable above the illumination system, and a tray holder, and wherein the tray holder receives the growth plate externally from the plate imaging unit and transports the growth plate along a single radial axis into the plate imaging unit to a focal alignment with the imaging device; a processor in electrical communication with the imaging device and having an image processing engine adapted to perform colony counting to monitor the biological growth, when present; a user interface in electrical communication with the reader and adapted to display a biological growth result display; and an alignment bracket having a lower fitting affixed to the illumination system and an upper fitting affixed to the imaging unit.

In some examples, the housing has a top imaging aperture. The imaging device may be aligned with the top imaging aperture. A fastener may semi-fix the lower fitting about the upper fitting. The lower fitting and upper fitting may be positioned together with at least one adjustment. The at least one adjustment includes an off-axis adjustment.

In particular examples, the tray holder receives and retains a growth plate having a recessed well with a sunken wall protruding below an upper face, a pair of opposing proximate extensions adjacent the recessed well and extending above the upper face, and a distal raised platform adjacent the recessed well and extending above the upper face. The tray holder may include a stationary end rotatably affixed to the baseplate. The tray holder may include a sunken support frame adapted to receive and retain the plate in a semi-fixed position. The tray holder may have a distal platform aperture, a well aperture, and pair of opposing proximate apertures are adapted to receive and mate with a corresponding inverted growth plate's recessed well, pair of opposing proximate extensions, and the distal raised platform.

In certain examples, a baseplate includes at least one mechanical backstop defining an alignment cradle to align the tray holder in a processing position. The illumination system may include an upper illumination dome having a plurality of light emitting diodes. Further, the illumination system may include a lower backlight diffuser.

In some examples, the reader, processor, and user interface are aligned substantially adjacent to one another on a bench top. Further, the reader, processor, and user interface may be integral with one another. The assembly may include at least one growth plate having a pair of opposing proximate extensions adjacent the recessed well and extending above the upper face, and a distal raised platform adjacent the recessed well and extending above the upper face.

Further embodiments include a method for monitoring biological growth, when present, on a growth plate comprises receiving at least one growth plate in a tray holder and transporting the growth plate into a focal alignment with an imaging device; selecting a plate type input chosen from at least a first plate type identifier and a second plate type identifier; imaging the growth plate with an imaging device positioned above the tray holder; and counting biological growth, when present, on the growth plate.

In particular examples, the first plate type identifier includes an aerobic count. The aerobic count may include lighting settings. In addition, the aerobic count may include imaging settings. The second plate type identifier may include an *E-coli* and coliform count, or the like. The *E-coli* and coliform count may include lighting settings. Further, the *E-coli* and coliform count includes imaging settings.

In certain examples, the method includes receiving the growth plate externally from a plate imaging unit. Further, the method may include transporting the growth plate along a single radial axis into a focal alignment with the imaging device. Counting biological growth may include marking bacterial colonies. In addition, marking may include circling bacterial colonies. For instance, the method may include displaying the circled bacterial colony counts on a user interface.

In some examples, selecting a plate type input includes manual selecting the plate type identifier on a user interface. Selecting a plate type input may include selecting a plate type identifier icon on a user interface. Further, selecting a plate type input may include voice commanding a selection of the plate type identifier.

In another embodiment, a reader for monitoring biological growth, when present, on a growth plate, comprises a plate imaging unit having an illumination system, an imaging device positionable above the illumination system, and a tray holder, and wherein the tray holder receives the growth plate externally from the plate imaging unit and transports the growth plate along a single radial axis into the plate imaging unit to a focal alignment with the imaging device; a user interface having at least two plate type identifiers; and a processor having an image processing engine adapted to perform colony counting to monitor the biological growth, when present, on the growth plate.

In particular examples, the first plate type identifier includes an aerobic count. The aerobic count may include a corresponding lighting setting. The aerobic count may include a corresponding imaging setting. The second plate type identifier may include an *E-coli* and coliform count. The aerobic count may include a corresponding lighting setting. The aerobic count may include a corresponding imaging setting. The user interface may include a graphical display of the biological growth counting, when present, on the growth plate.

In some examples, the plate imaging unit may include a baseplate substantially parallel to the tray holder. The baseplate may include at least one mechanical backstop defining an alignment cradle to align the tray holder in a processing position. The baseplate may include a backlight indent adapted to receive a backlight. The tray holder may include a stationary end rotatably affixed to the baseplate. The tray holder's stationary end may include a bearing. The tray holder may include a sunken support frame adapted to receive and retain the plate in a semi-fixed position. The tray holder may include a recessed distal platform aperture, a recessed well aperture, and a pair of opposing proximate apertures. The growth plate may include a recessed well having a sunken wall protruding below an upper face, a pair of opposing proximate extensions adjacent the recessed well and extending above the upper face, and a distal raised platform adjacent the recessed well and extending above the upper face. The tray holder's distal platform aperture, well aperture, and pair of opposing proximate apertures may receive and mate with a corresponding inverted growth plate's recessed well, pair of opposing proximate extensions, and the distal raised platform.

In another embodiment, a plate imaging unit for imaging biological growth, when present, on a growth plate, the unit comprising: an illumination system, including an upper illumination dome having a plurality of light emitting diodes and a lower backlight diffuser; a base plate including a backstop and an opposing open portion; a tray holder including a sunken support frame adapted to receive and retain an inverted plate in a semi-fixed position, a stationary end rotatably affixed to the base plate, and a traversing end adapted to allow entry and exit into the base plate along a single radial axis; and a plurality of plate type identifiers.

In a further embodiment, a plate imaging unit for imaging biological growth, when present, on a growth plate includes a mounting foundation; a base plate; a backlight diffuser positioned between the mounting foundation and the base plate, a tray holder coplanar with base plate, and wherein the tray holder having a stationary end rotatably affixed to the base plate and a traversing end to allow entry and exit from the unit along a single radial axis; an illumination dome having a plurality of light emitting diodes positioned above the base plate; and a high resolution camera centered above the illumination dome.

In particular examples, the mounting foundation includes a plurality of couplers adapted to affix the base plate. The baseplate may include a backstop and an open front portion, thereby defining an alignment cradle to align the tray holder in a processing position. The baseplate may include an optics aperture. The baseplate may include a protruding mounting portion to rotatably retain the plate holder's stationary end.

In certain examples, the tray holder includes a body supporting a sunken support frame to retain the plates in a semi-fixed position. The tray holder may include an extension neck protruding from the body and supporting an alignment assembly. The extension neck may include a spring plunger catch and the alignment assembly includes a support block, a ball knob, and a plunger aligning the ball knob about the support block.

In some examples, the assembly includes an image processor that is operably connected to a high resolution camera. The processor may be housed in a laptop computer, tablet, or the like. The processor may have image inputs and pipeline parameter inputs. In some examples, the parameter inputs include calibration inputs and/or fixed inputs based on specific plates.

In another embodiment, a reader for monitoring biological growth, when present, on a growth plate, includes a plate imaging unit and a processor. The plate imaging unit may have an illumination system, an imaging device positionable above the illumination system, and a tray holder, and wherein the tray holder receives the growth plate externally from the plate imaging unit and transports the growth plate along a single radial axis into the plate imaging unit to a focal alignment with the imaging device. The processor may have an image processing engine to perform colony counting to monitor the biological growth, when present, on the growth plate.

In certain examples, the plate imaging unit includes a baseplate that is substantially parallel to the tray holder. The baseplate may include at least a first stop and an adjacent second stop defining an alignment cradle to align the tray holder in processing position. The baseplate may include a backlight indent adapted to receive a backlight. The tray holder may include a stationary end rotatably affixed to the baseplate. The tray holder's stationary end may include a bearing. The tray holder may include a sunken support frame adapted to receive and retain the plate in a semi-fixed position. The tray holder may include a recessed distal platform aperture, a recessed well aperture, and a pair of opposing proximate apertures.

In particular examples, the growth plate includes a recessed well having a sunken wall protruding below an upper face, a pair of opposing proximate extensions adjacent the recessed well and extending above the upper face, and a distal raised platform adjacent the recessed well and extending above the upper face. The tray holder's distal platform aperture, well aperture, and pair of opposing proximate apertures may receive and mate with a corresponding inverted growth plate's recessed well, pair of opposing proximate extensions, and the distal raised platform.

In a further embodiment, a plate imaging unit for imaging biological growth, when present, on a growth plate, may include an illumination system, including an upper illumination dome having a plurality of light emitting diodes and a lower backlight diffuser; a base plate including a backstop and an opposing open portion; and a tray holder including a sunken support frame adapted to receive and retain an inverted plate in a semi-fixed position, a stationary end rotatably affixed to the base plate, and a traversing end adapted to allow entry and exit into the base plate along a single radial axis.

In yet a further embodiment of the present disclosure a reader for semi-continuously monitoring biological growth on a growth plate includes an illumination system illuminating a top and side of the growth plate; an imaging device positionable above the illumination system; and a drawer assembly spaced below the illumination system and to transport the growth plate along a single axis into the reader to a focal alignment with the imaging device and eject the growth plate from the reader. Typically, the imaging device semi-continuously monitors an isolated area of interest on the growth plate.

In some examples, the illumination system is a light box including a perimeter lighting frame having a first, second, third and fourth light sides, the first and second sides opposing one another and the third and fourth sides opposing one another and the first and second sides being substantially perpendicular to the third and fourth sides. Further, the perimeter lighting frame may include a plurality of light emitting diodes. The perimeter lighting frame may include a diffuser to soften light emitted from the light emitting diodes on the growth plate. The perimeter lighting frame may focus light on a top and at least one side of the growth plate.

In particular examples, the drawer assembly includes a slide support face. The drawer assembly may include a raised boundary on opposing sides of the slide support face. The drawer assembly may include opposing walls adjacent the boundary. The drawer assembly may include a traversing tongue to secure the growth plate.

The reader may include a mounting akin supporting the imaging device. The imaging device may be a video image capture device. The video image capture device may be a USB camera. The imaging device may image the growth plate in multiple quadrants. The imaging device may image the growth plate as a whole. Further, the image processor may be operably connected to the imaging device.

Another embodiment of the present disclosure is an optical bench having an upper housing having a light box; and a lower housing having a drawer assembly externally receiving and transporting the growth plate, for instance into the reader to a focal alignment with the imaging device and eject the growth plate from the reader. Typically, the light box substantially encloses the growth plate and the drawer assembly aligns the growth plate in substantially fixed focal length distance within the imaging device's field of vision.

In some examples, the imaging device performs a semi-continuous imaging of an isolated area of interest on the growth plate. The growth plate may include a reference grid, wherein the imaging device uses the reference grid to navigate and provide a plurality of pixel map images of the fixed area for monitoring bacterial colony development. For instance, the imaging device may generate a pixel map on the growth plate, whereby the pixel map is an indication of the biological development when present. The growth plate may include a plurality of quadrants having a plurality of pixel map values. The pixel map value may be a prediction of a final test result prior to the test result being visible to the human eye. Further, the pixel map value may be an observation of early stage biological development.

In particular examples, the light box includes a light perimeter frame. The light perimeter frame may include a plurality of light emitting diodes. The light perimeter frame may include a diffuser to soften light emitted from the light emitting diodes on the growth plate. Further, the light perimeter frame may focus light on a top and at least one side of the growth plate.

In some examples, the drawer assembly is moveable along an axis to allow entry and exit from the reader. The drawer assembly may include a slide support face. The drawer assembly may include a raised boundary on opposing sides of the slide support face. The drawer assembly may include opposing walls adjacent the boundary. The drawer assembly may include a traversing tongue adapted to secure the growth plate. The optical bench may include a mounting arm supporting the imaging device. The imaging device may be a video image capture device, for instance a USB camera.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
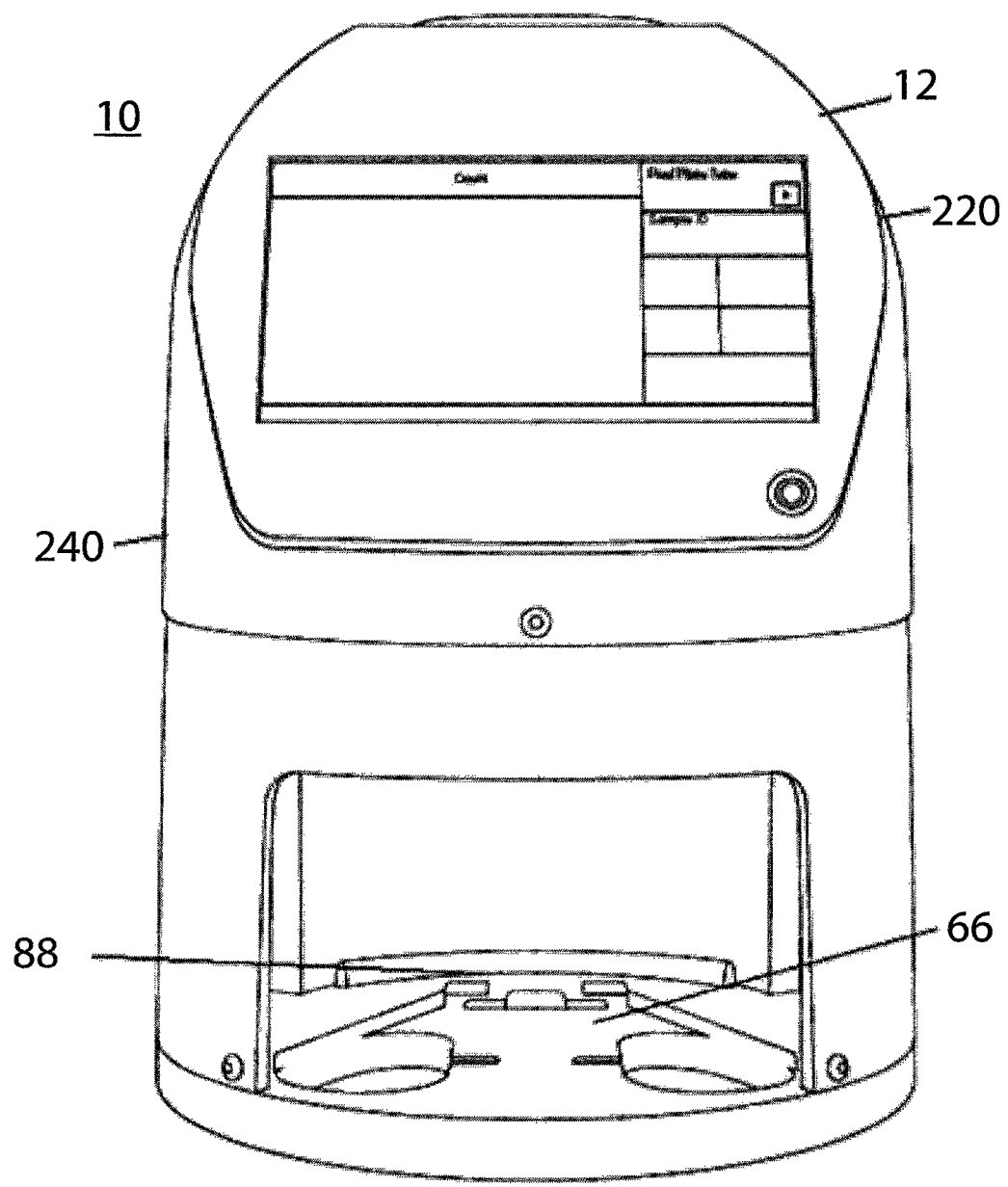
FIG. 1 is a front view of one embodiment of a plate reader according to the present disclosure.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general, it will be understood that the illustrations are for the purpose of describing embodiments of the disclosure and are not intended to limit the disclosure or any invention thereto. The reader system 10 and assemblies are shown embodied according to the present disclosure to observe and monitor imaging and to provide increased sample throughput, direct data results reporting, and processed plate image storage. The reader generally images biological development, when present, on an individual growth plate 20 and/or a plurality of growth plates 20, or similar testing medium. The assembly generally monitors imaging development on at least one image of the growth plate, alerts results and counts, and quantifies biological growth, when present.

FIGS. 1-2, 3, and 6 illustrate embodiments of a plate reader to generally receive, image, and count microbial colony growth, when present. These assemblies include plate imaging, processing, and user interface elements, either in electrical communication with one another or combined into an integral assembly, as understood by those of ordinary skill in the art having the benefit of this disclosure.

Figure 4:
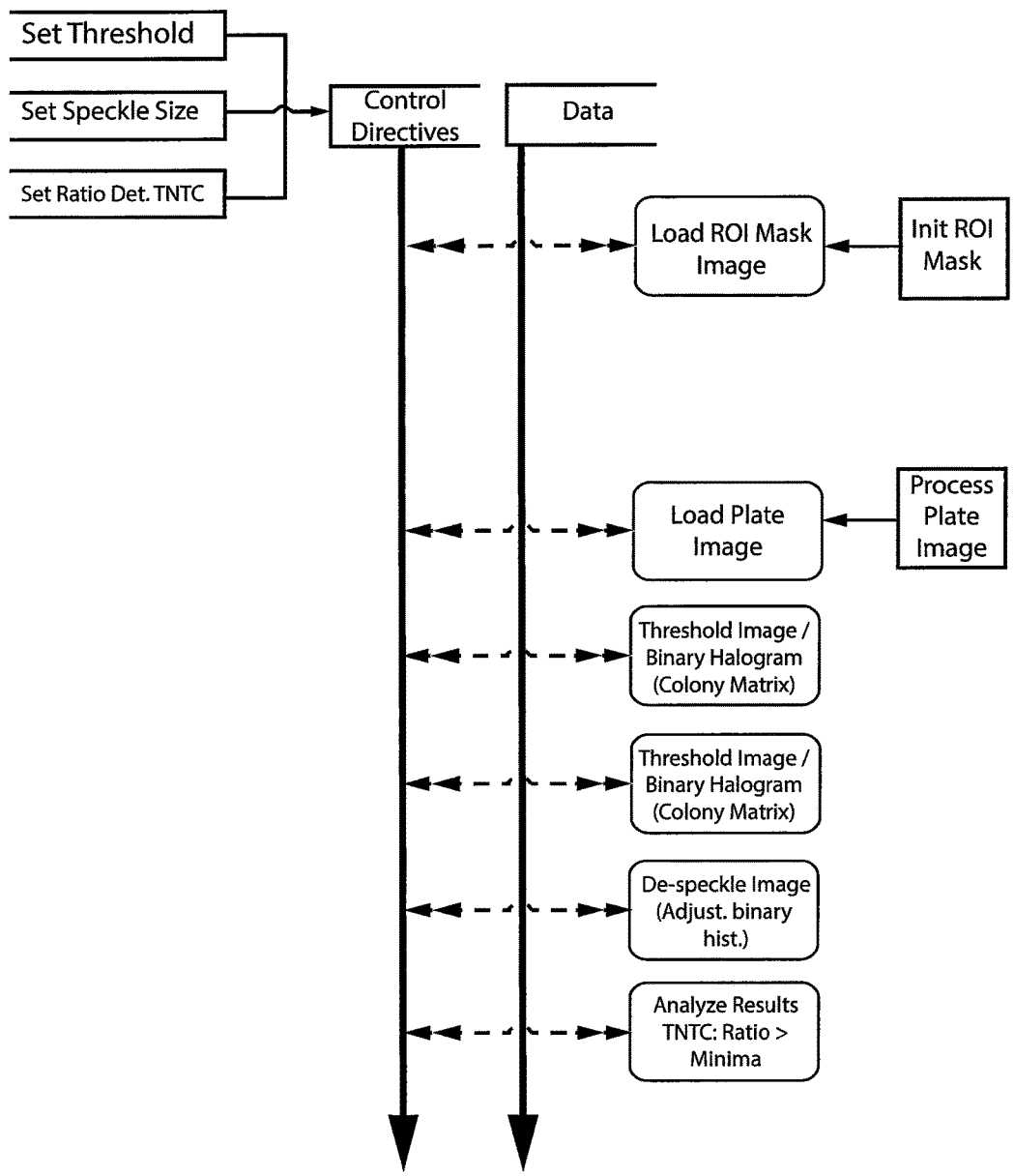
FIG. 4 is a schematic view of one example of too numerous to count (TNTC) process diagram, with elements and steps removed for clarity of the example.
Figure 6:
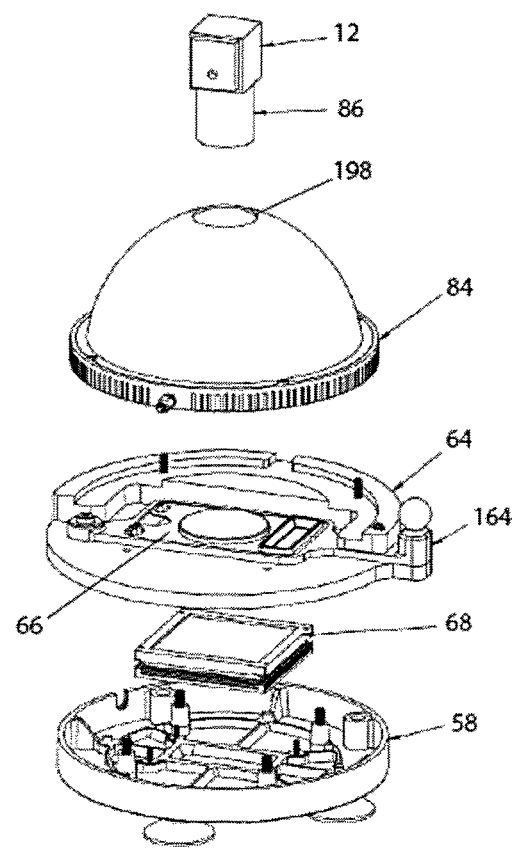
FIG. 6 is an exploded perspective view of particular system elements.

In certain embodiments, housing features and a variety of outer supports align and shield internal components. For instance, as shown in FIG. 1, an outer housing 240 surrounds internal imaging and processing components to generally define an integral system. The housing 240 may include a plurality of openings to allow access to the plate nest frame and like elements shown and described herein. As shown in FIG. 6, useful, although not necessarily required in every embodiment, elements housed within housing 240 may include a mounting foundation 58, a backlight diffuser 68, a base plate 64, a portion of a nest frame 66, an illumination dome 84, and an optics imaging device 12. As shown in FIGS. 4 and 6, the illumination dome 84 may include an optics enclosure 198 to generally enclose the imaging device 12. The illumination dome 84 may evenly illuminate the plates and prevent reflections on the plate surface.

Figure 3:
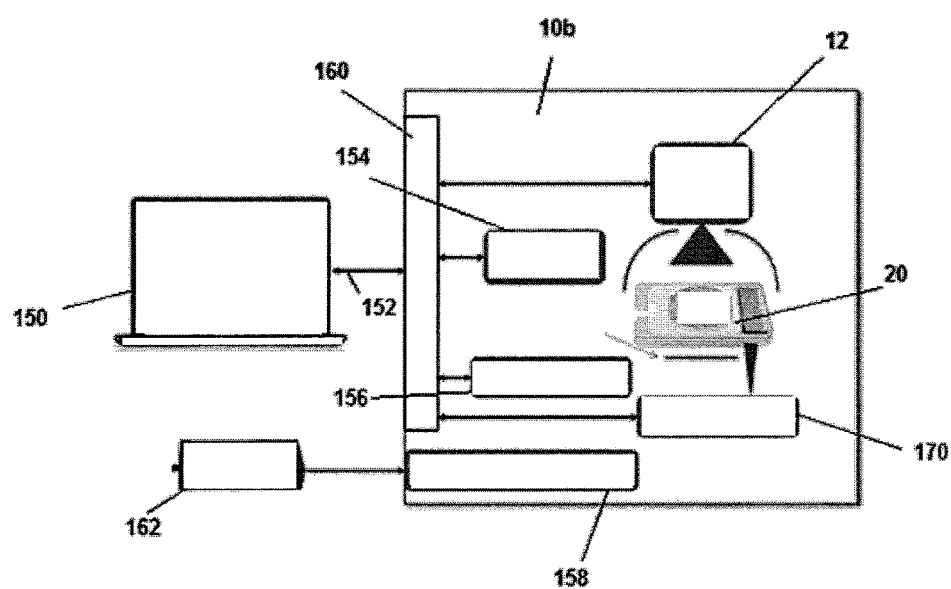
FIG. 3 is a schematic view of a plate reader assembly according to one embodiment of the disclosure.
Figure 3A:
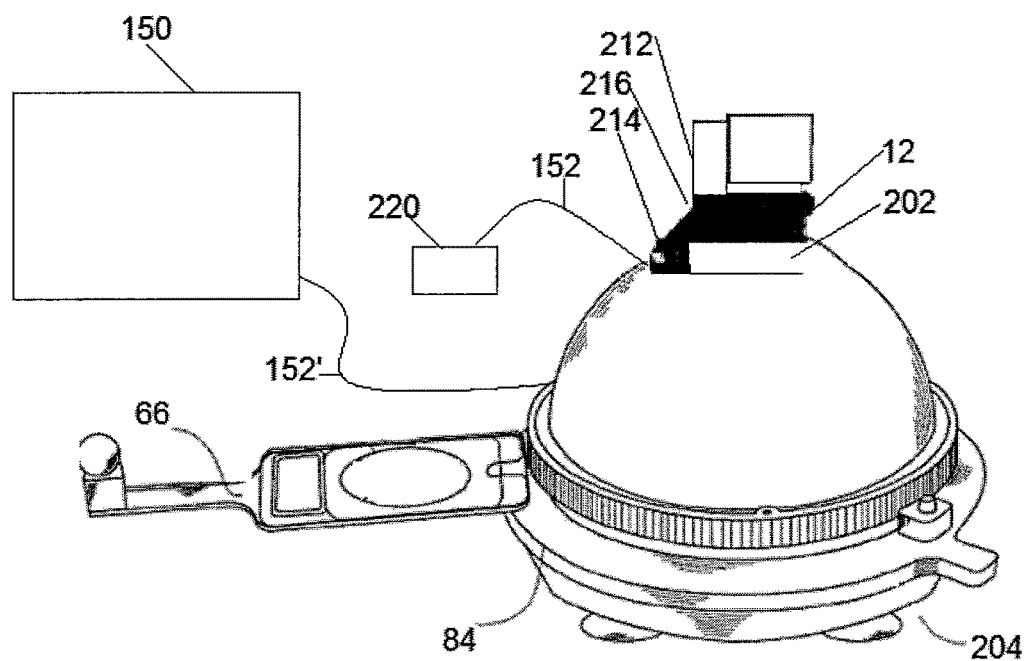
FIG. 3A is a perspective view of a plate reader assembly according to one embodiment of the disclosure.

FIGS. 3 and 3A illustrate examples of a non-integral readers having a plate imaging unit and reader system in data communication with a computer processor 150. The assembly typically includes an image processing engine to perform colony counting to count and/or monitor biological growth, including microbial colony counting, bacterial counting, and the like, when present, on the growth plate. In particular examples, the computer processor 150 is a qualified laptop, tablet, or the like running plate analyzer processing described and shown herein.

As shown in FIGS. 1, 3, 3A, and 6, the reader system may include an imaging device 12 adjacent to the plate 20 in an imaging position. An alignment bracket(s), frame, and the like may secure any of elements shown and described herein in a semi-fixed position. For instance, a lower fitting 214 may be affixed to the illumination system, housing, or the like. Similarly, an upper fitting 212 may be affixed to the imaging unit, devices, housing, or the like. The lower fitting 212 and upper fitting 214 may be secured about one another in a variety of configurations and alignments, including, but not limited to, with a fastener 214 or similar linkage. The lower fitting 212 and upper fitting 214 may be positioned together with at least one adjustment. In certain examples, the adjustment includes an off-axis, i.e. a horizontal, vertical, or the similar, adjustment.

The system may include sensors 154 to indicate any of the alignment and/or alert system errors shown and described herein. Further, the system may include illumination control 156 to control any of the illumination elements and aspects herein. In addition, the system may include power distribution 158 to control and distribute power for any of the elements and aspects shown and described herein, and a power supply 162, including but not limited to an external power supply. Certain reader system elements are in electrical communication with a user interface, for instance computer processor 150, via a unified communication interface 160 and/or USB connection 152, 152' or the like. Those skilled in the art having the benefit of this disclosure will recognize additional orientation of components in electrical communication, including alternative integral and non-integral arrangements of imaging, processing, and display elements herein.

In particular examples, the method may include a prefilter step, followed by a threshold step, and followed by a histogram analysis step to trigger any of the TNTC error messages shown and described herein. The analysis may include setting a threshold, setting a speckle size, and setting a too numerous to count ratio. As shown in FIG. 4, the control generally directs analysis of the data to generate an output of percent ration of colony/matrix, for example a TNTC threshold ratio determination. The system control may initiate loading a region of interest (ROI) as shown and described herein. In particular examples, the ROI may represent a processing region, for instance a circled portion or the like. The system control may load a ROI mask image, and may initiate a ROI mask. The system control may threshold the image using a histogram process of the plate image may determine an appropriate percentage of the plate image being identified as background and non-background. In this way, any of the systems and readers herein may compare background values identified on a plate to a value of an object identified on a plate, i.e. brightness, size, or the like, in the plate image to indicate the result may be too highly populated with non-background data. In particular examples, a weight factor may be applied to consider count size as a determination that the result, i.e. the colony or the like, has reached a critical size, thus causing an accurate count to be less reliable. For instance, the count may have a weight associated with the count based on size, i.e. more than the identification of the existence of the colony. In yet further embodiments, the methods may include a cascade vertical and horizontal histogram analysis to identify individual colonies, or the like, of interest. Those of ordinary skill in the art having the benefit of the disclosure will recognize additional methods and operations for identifying any of the TNTC, or similar alert counts, shown and described herein.

Figure 10:
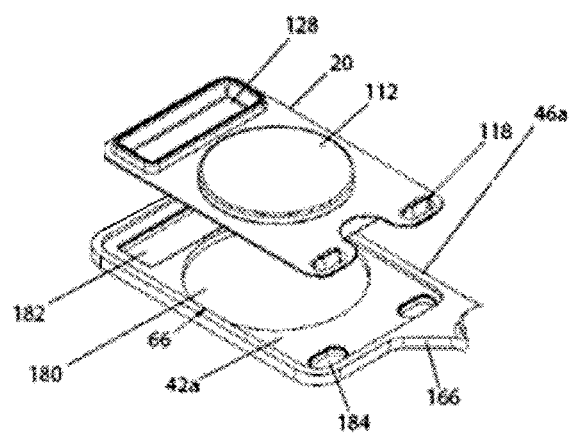
FIG. 10 is an isolated, top perspective view of an embodiment of a frame nest and corresponding plate.

FIG. 10 shows one example of a partially exploded nest frame for illustrating internal alignment components within the assembly as generally shown and described herein. As previously shown in FIGS. 1A and 2, a user may manually load the plate into the nest frame (including aligning any of the growth plate features with any of the frame support features shown and described herein) into a focal alignment with an imaging device in the reader system.

Figure 1A:
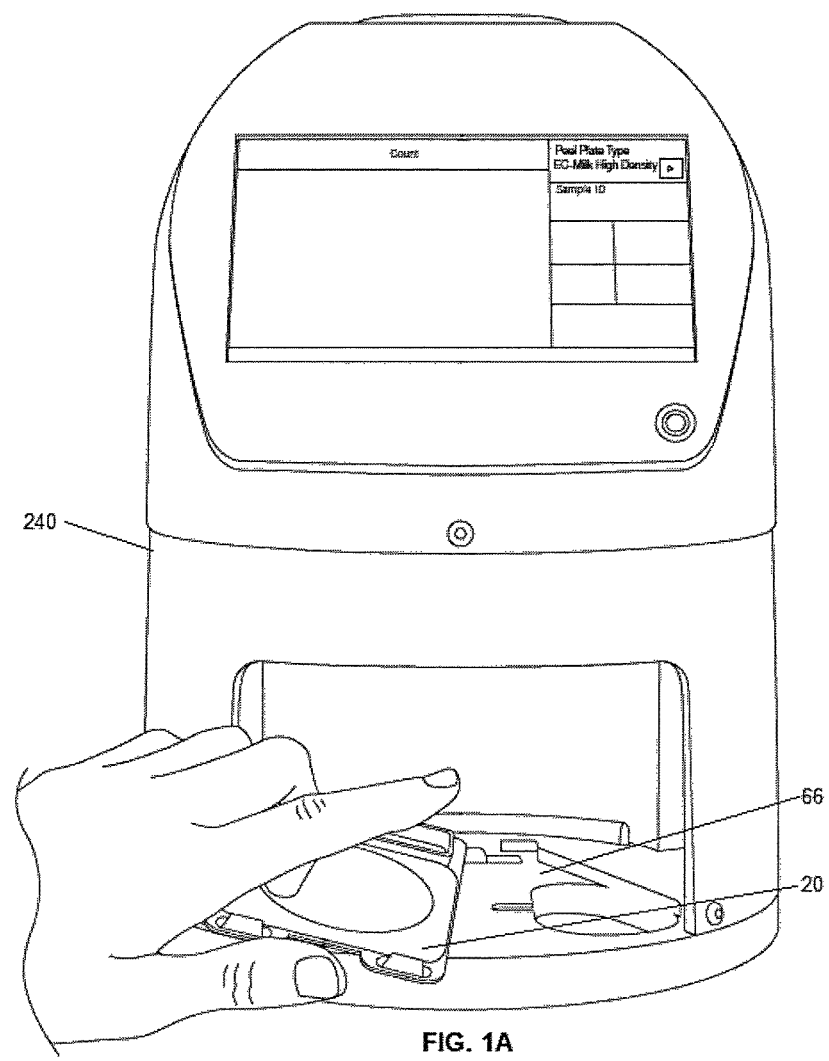
FIG. 1A is a front view of one example of loading a plate into the plate reader introduced in FIG. 1.
Figure 2:
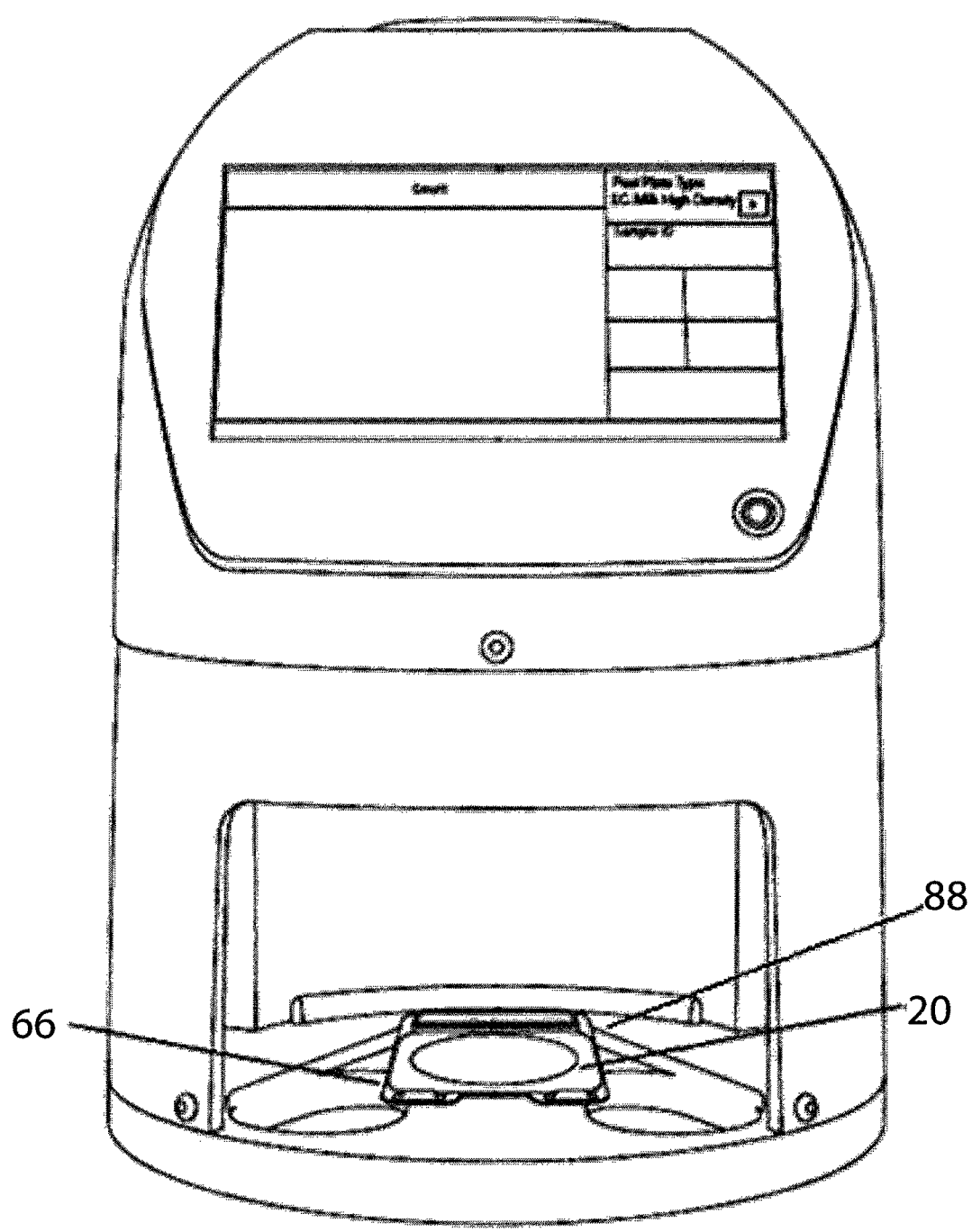
FIG. 2 is a front view of the plate reader introduced in FIG. 1 in a loaded, operating position.

Operation of the assembly may be triggered in a variety of ways, including, but not limited to, manual selection on a user interface, voice activation, remote or timed start, manual positioning of the plate, and the like. FIG. 1A shows one example of a manual positioning of the plate.

Figure 11:
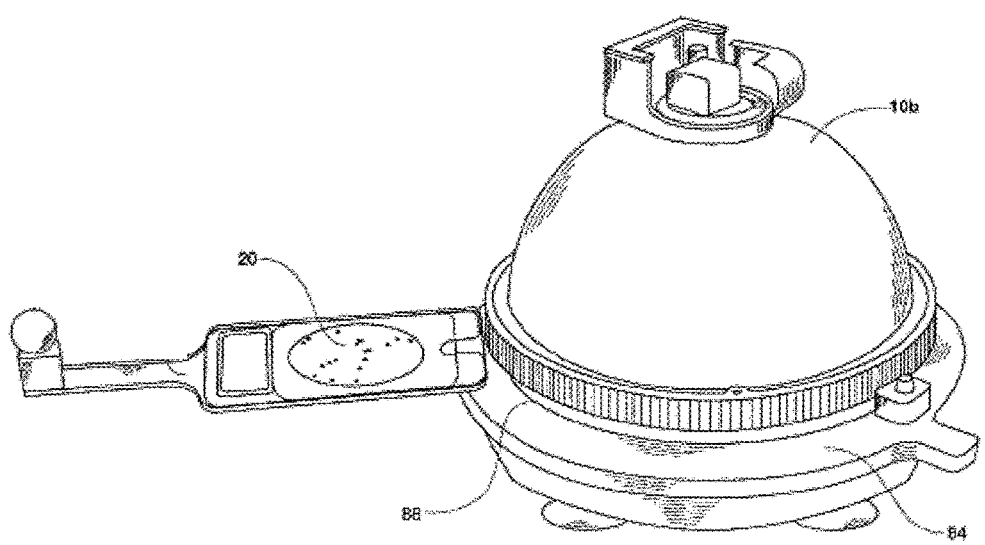
FIG. 11 is front perspective view of another plate reader system embodiment loaded with one example of a peel plate.

In alternative embodiments, as shown in FIG. 11, a tray holder 66 may include a traversing end 164 that transports plates along a single radial axis along track 88. The tray holder may comprise any of the reader nest frames shown and described herein. In these alternative examples, for instance as illustrated in FIG. 11, a user may manually load the plate into tray holder 66 (including aligning any of the growth plate features with any of the tray holder features shown and described herein) which is extending from the device, i.e. is outside and adjacent imaging aspects of the device. The user may then manually transport the tray holder 66 into the device, for instance manually transport along a fixed axis 200 into a focal alignment with an imaging device in the reader system. In certain examples, the tray holder 66 snaps into place with a position bearing to confirm a centered position with the imaging device within the reader system.

Figure 5:
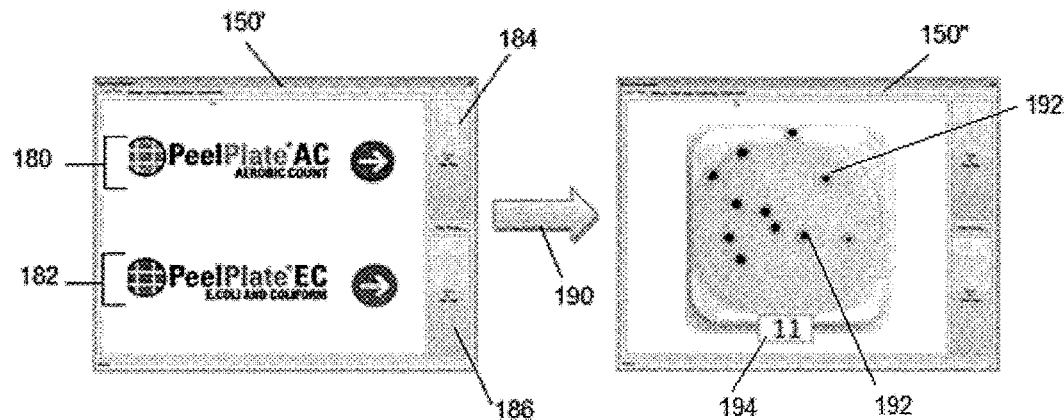
FIG. 5 is a screen view of one embodiment of a plate type selection.

In use, the operator manually selects the proper plate and count operation to be performed by the assembly. As shown in FIG. 5, one example of the user interface selection screen 150' includes a first plate type identifier 180 and a second plate type identifier 182. In other examples, the selection screen 150' includes a plurality of plate type identifiers, including three or more identifiers. The operator may manually select the plate type identifier by selection, clicking, touching, or the like, the proper icon, voice activating the assembly to types of plates to count, or similar selection processes. As shown in FIG. 5, the user interface 150' may include a first plate count input selection 184 and a second plate count input selection 186. Again, other examples of the selection screen 150' includes a plurality of other manual plate type count input selections.

In particular examples, the first plate type identifier 180 includes an aerobic count used for the detection and enumeration of aerobic bacteria in dairy and food decimal dilutions. The aerobic count may include lighting settings, imaging settings, and similar counting settings. The second plate type identifier 182 may include an *E-coli* and coliform count used for detection and enumeration of coliform bacteria, including *E-coli* in dairy, food, and water. Again, the *E-coli* and coliform count may include lighting settings, imaging settings, and similar counting settings. Another plate type identifier may include a yeast and mold count used for detection and enumeration of yeasts and/or molds in foods and environment. In addition, another plate type identifier may include a heterotrophic plate count used for detection and enumeration of water samples.

In certain examples, a user selects a plate type (including any of the plate type selections shown and described herein). The user may load a blank plate for quality control assurance and/or calibration as described herein. The device may then capture an image of the blank plate. In certain examples, the image is stored on a storage device, hard drive, or the similar means. The user then manually loads the plate with the sample and selects the count plate indicator to initiate a particular sequence, i.e. typically the plate is manually loaded and the indicator is selected prior to imaging the plate. The imaging device may capture one, or multiple frames averaged together for greater consistency, to create an image using pixel-to-pixel averages for noise reduction of frames. In some examples, the device may set a plate identification, for instance by reading barcode or the like. The system may verify a plate diameter to ensure a proper plate is being analyzed. In particular examples, the system checks the diameter of the plate to verify a proper plate is seated in the system, including, but not limited to, monitoring if the plate is properly seated and an edge is visible to trigger an out of position message.

In particular examples when the second plate type identifier 182 for an *E-coli* and coliform count is selected, the system loads average and background images. The system may then crop an average image to yield an image of active portions of the pate as recognized by those skilled in the art having the benefit of this disclosure. The system may then crop background image, divide the average image by the background image to yield background-subtracted image. The system may then invert the image and threshold the image in any of the methods shown and described herein. The system identifies primary objects, including colonies. The image may then be cropped again, and the color objects may be unmixed. For instance in the *E-coli* and coliform count, the system separates (unmixes and the like) and counts the red color counts and the blue color counts. In particular examples, the results are recorded and saved to a database by any of the procedures described herein.

Similarly, when a first plate type identifier 180 for an aerobic count used for the detection and enumeration of aerobic bacteria is selected, the system loads average and background images. The system may then crop an average image to yield an image of active portions of the pate as recognized by those skilled in the art having the benefit of this disclosure. The system may then crop background image, divide the average image by the background image to yield background-subtracted image. The system may then mask colors of the imagery, typically the mask may be defined in the graphical user interface. The color objects may be unmixed. The system then thresholds the image in any of the methods shown and described herein. The system identifies primary objects, including colonies. In particular examples, the results are recorded and saved to a database by any of the procedures described herein. Those skilled in the art will recognize additional operations and methods, including any image counting method 190, triggered by a selected plate type with the benefit of this disclosure.

In particular examples, the user interface display 150" presents a count result 194. The user interface display 150" result may include marking bacterial colonies. For instance, as illustrated in FIG. 5, the display 150" may present circled bacterial colony counts 192 on an image of the plate, or the like. The processed image 150" may include a coded name, for instance marked on a barcode or the like as described herein, and a CSV file with corresponding colony count information. The output image and an output report will vary depending on the type of plate being processed. For example, an aerobic count may indicate a unified count of all colonies, whereas an *E-coli* count contain color categorized colonies.

FIG. 6 illustrates useful internal elements, for instance base plate 64 and mounting foundation 58 assembly. The mounting foundation may include one or a plurality of supports 138, including suction cups, fittings, braces, and the like, to support any of the plate imaging units shown and described herein about a flat surface or similar laboratory bench. Fasteners 139, 156, and 148, as well as grommet 152 and spring plunger 154 may secure the base plate 64 about the mounting foundation 58 and/or other bodies. Further, a backlight diffuser, for instance the backlight box 68 may be positioned between the base plate 64 and mounting foundation 58 to generally diffuse flat lighting under the plate to enhance silhouette detection.

Figure 7:
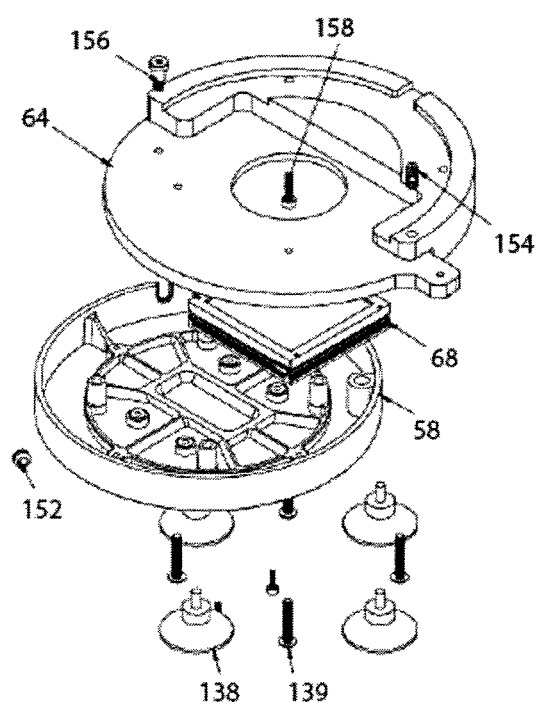
FIG. 7 is an exploded perspective view of the system shown in FIG. 1 with elements removed for clarity.
Figure 8:
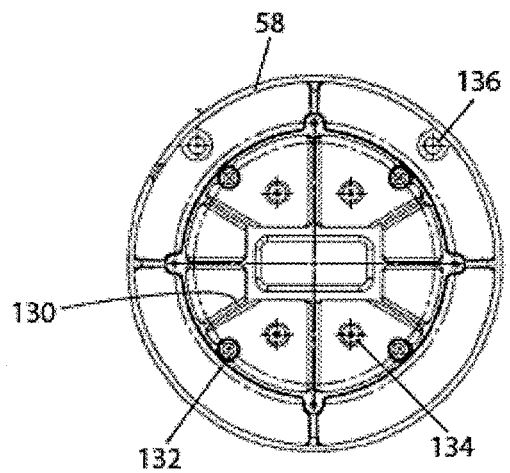
FIG. 8 is an isolated, top view of a mounting foundation shown in FIG. 7.
Figure 9:
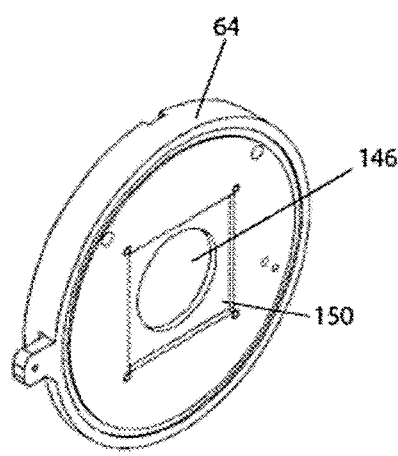
FIG. 9 is an isolated, top perspective view of a base plate shown in FIG. 7.

FIG. 7 shows one example of mounting foundation 58 of the image station for supporting the plate imaging unit. The mounting foundation 58 may include one or more mounting holes 136 to mate with the base plate 64. Further, the mounting foundation 58 may include a foundation framing 130, or similar solid supporting, to support the load of any of the elements and examples shown and described herein. The mounting foundation 58 may include base plate couplers 132 and backlight diffuser couplers 134 so support and provide clearance for foundation and lighting elements. Those of ordinary skill in the art having the benefit of this disclosure will recognize additional framing and support elements and alternatives.

FIG. 6 illustrates one example of a baseplate 64 to generally align plate frame nests. For instance, any of the reader devices herein may include a frame nest support to generally receive and retain any of the plates during operation and the like. As shown in FIG. 10, a receiving nest may include a sunken support frame 42a surrounded by a raised boundary 46a, thereby providing a cavity to receive and retain the plates. In particular examples, the support frame 42a may include a recessed distal platform aperture 182, a recessed well aperture 180, and a pair of opposing proximate apertures 184 to mate with a corresponding inverted growth plate's recessed well, pair of opposing proximate extensions, and distal raised platform as shown and described herein. An attachment portion 166 may align the frame nest about any internal structure, for instance within the housing. Further, an optics aperture 146 may be aligned in the alignment cradle 140. In one example, a backlight indent 150 mates with the backlight 68 centered on the optics aperture 146.

Any of the reader devices herein may include a frame nest support to generally receive and retain any of the plates during operation and the like. As shown in FIG. 10, a receiving nest may include a sunken support frame 42a surrounded by a raised boundary 46a, thereby providing a cavity to receive and retain the plates. In particular examples, the support frame 42a may include a recessed distal platform aperture 182, a recessed well aperture 180, and a pair of opposing proximate apertures 184 to mate with a corresponding inverted growth plate's recessed well, pair of opposing proximate extensions, and distal raised platform as shown and described herein. An attachment portion 166 may align the frame nest about imaging elements, for instance within the housing.

Those of ordinary skill in the art having the benefit of this disclosure will recognize that any of the growth plates shown and described herein may include plate-like devices, Petri dish culture devices, and the like. Typically, the growth plate 20 includes a growth area where biological growth, or the like, may develop. As shown in FIGS. 12-15 the growth area may be transparent and may have a recessed well that is useful for culturing various microorganisms.

Figure 12:
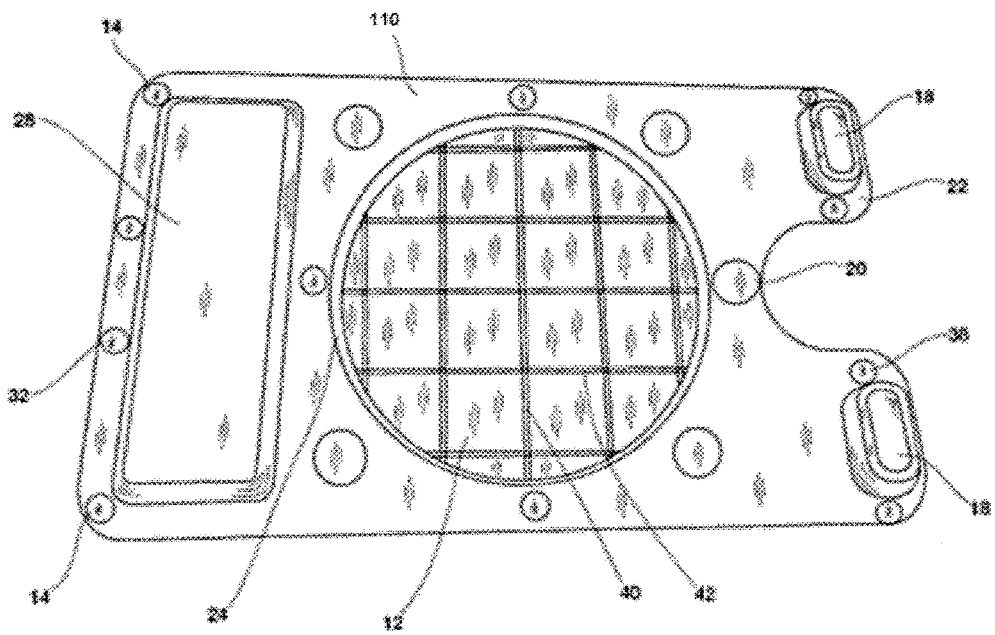
FIG. 12 is a top perspective view of one embodiment a peel plate.

FIG. 12 introduces one example of a culture device peel plate 110 for enumerating and/or detecting a microorganism from a sample that is useful for the reader examples and embodiments shown and described herein. The peel plate 110 typically is a semi-rigid waterproof plate onto which sample may be applied to enumerate microorganisms and the like. As seen in FIG. 12, one example of the peel plate 110 includes a recessed well 12, a distal raised platform 28, and opposing proximate tabs 22 having proximate extensions 28 to support stacked plates as shown and described herein. The upper face 14 of the plate typically has a top periphery 32 around the raised platform. The recessed well 12 includes a sunken wall 24 below the upper face 14. As shown in FIG. 12, the recessed well may include a grid, for instance having vertical line 40 and intersecting horizontal line 42 components useful for colony counting. In particular examples, the grid is molded, printed, and the like on the rear surface. The grid may be printed in a variety of ways, including inkjet printing, pad printing and the like. Regardless of the grid type, the grid is typically visible through the generally transparent culture device to the front surface and/or rear surface. The plate 110 is also typically transparent material so as to enable observation from the outside, including any of the printed grids shown and described herein.

FIG. 12 further shows the proximate end of the peel plate 110 includes an access indent 20 with opposing proximate tabs 22 between rounded corners 38. Typically, the proximate tabs 22 offset the proximate extensions, and the like, from the body of the plate, i.e. the well and the majority of the upper surface. Thereby the proximate tabs include proximate extensions 18 for alignment, stability, and support during testing/usage, including, but not limited to, layering and stacking plates in any of the arrangements and orientations shown and described herein.

Figure 13:
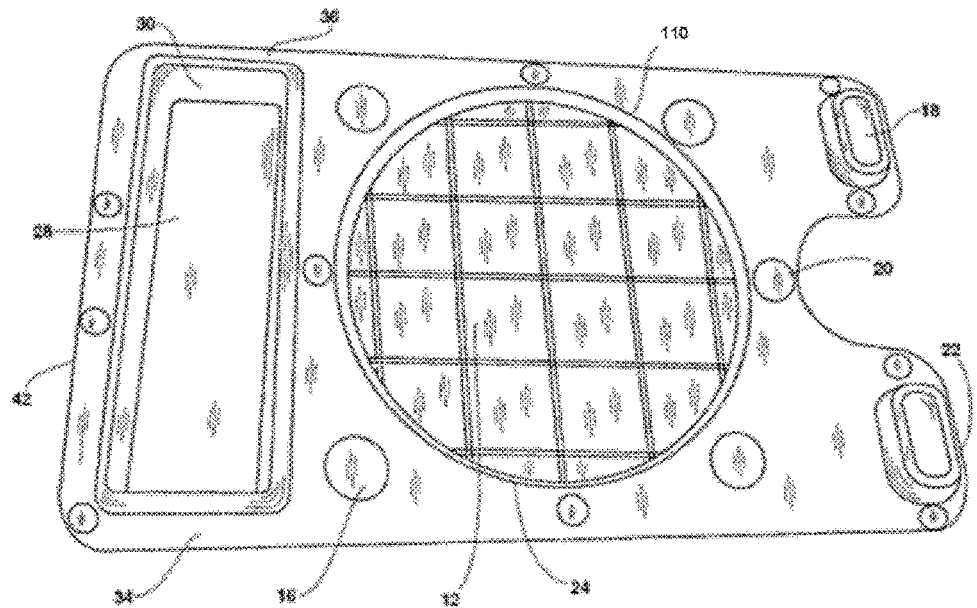
FIG. 13 is a bottom perspective view of the peel plate introduced in FIG. 12.
Figure 14:
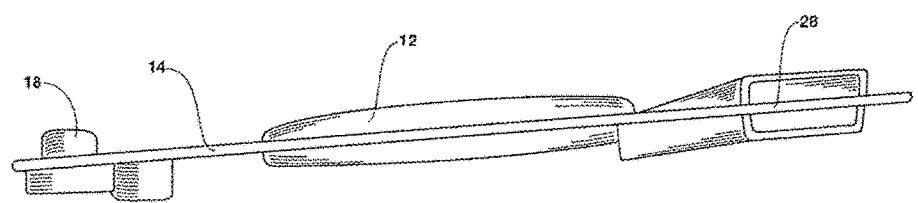
FIG. 14 is a side perspective view of the peel plate introduced in FIG. 12.

FIGS. 13 and 14 show a bottom and side view, respectively, of one example of a peel plate 110 having a raised edge 30 extending above the lower face 16 to define the raised platform 28. Typically, the peel plate has a distal thickness 42 to support any of the elements and testing procedures shown and described herein.

Figure 15:
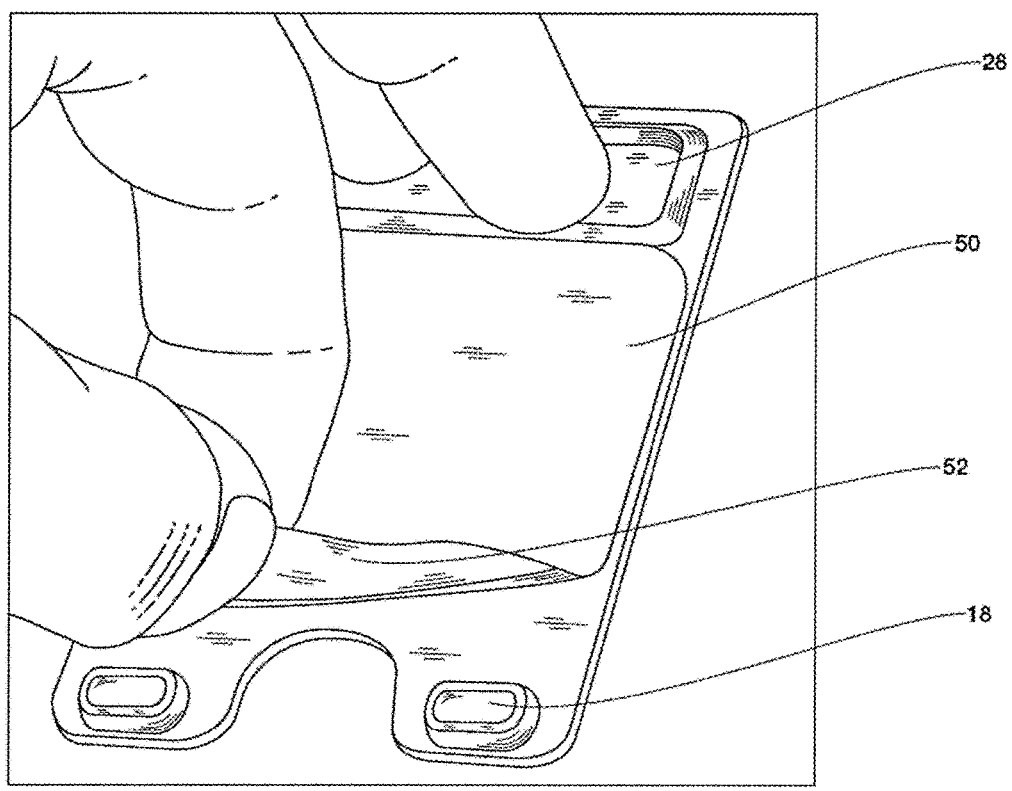
FIG. 15 is a side perspective view of a peel plate and singular, planar peel.

FIG. 15 introduces one example of a peel plate 110 having a covered surface as shown and described herein. For instance, the peel plate 110 may be placed on a substantially level surface. The peel tab 52 may be lifted concurrently while pressure is applied to the raised platform 28 with the user's fingers, or the like. In particular examples, the tab 52 may be lifted vertically upwards and away to expose any of the culture media shown and incorporated herein. In particular the culture media is any of the dried media culture disc shown and described herein.

The processors described herein are typically in electrical communication, including USB connection, wireless, or the like, with the plate imaging unit. The processor may include an image processing engine to perform colony counting operations and the like. In particular examples, the image processing engine has image inputs and pipeline parameter inputs. Particular parameter inputs are determined by calibration, including any of the calibration steps and examples herein. Other fixed plate type parameters may be fixed. The image processing engine may generate a variety of outputs, for instance colony counting information.

In particular embodiments, any of the reader devices and systems herein may identify statistically unexpected interpretations, imagery, or identify particular observations, and indicate an alert message. For instance, as illustrated in FIG. 4, the reader may indicate an alert to perform a manual determination with a count identified has having larger than selectable size.

In some embodiments, the reader may recognize a spreader colony as understood by those skilled in the art having the benefit of this disclosure and deliver a spreader-manually check message, or the like. For instance, the system may identify a plurality of large size particulates and group them as a spreader colony or the like. For instance, the reader may identify unexpected large colony counts, generate a spreader colony interpretation, and allow the user to override the alert message. Further, if the reader identifies too numerous to count results as understood by those skilled in the art having the benefit of this disclosure, the reader may display a too numerous to count (TNTC) alert message or similar error message.

In alternative embodiments, the plate imaging unit may include an optics bench. In this example, the optics bench includes an upper housing and a lower housing. The upper housing may include an illumination system, for instance the light box, and an adjustment assembly. The lower housing may include a drawer opening having a slide support frame being repositionable about alignment assembly. The slide frame may secure a support tongue, a raised boundary on opposing sides of the support tongue, and adjacent opposing walls. The support tongue generally secures the peel plate in a semi-fixed position during alignment and operation.

Further, in alternative embodiments an imaging device may be aligned above the illumination system substantially surrounding the growth plate. The optics may be any of the imaging devices shown and described herein, including a camera to capture any of the still and video images supported by optics communication.

In some examples, the camera includes a moveable lens to manipulate the focal distance of the imaging device to capture a variety of pixel mappings. For instance, the camera lens may be moved closer to the plate or more distant from the plate to gather a variety of pixel mappings, depending on the particular testing sequence.

In some examples, the illumination system includes a plurality of light emitting diodes (LEDs), for instance ninety six, or the like, white LEDs. The light box may include a perimeter lighting frame having a first, second, third and fourth light sides to provide focused light on the top and sides of the peel plate. Further, the light box may include a diffuser.

In yet another alternative example, an imaging device is positioned on the mounting arm about the upper face of the housing. Those of ordinary skill in the art having the benefit of this disclosure will recognize the imaging device may include any optics electronics processing board. Further, the reader may include a processor to provide any of the imaging and analysis shown and described herein.

The vision system for any of the imaging devices shown and descried herein may utilize a grid, reference lines, markings, quadrants, and the like for consistent mapping of specified locations on and among the plates. Further, any of the imaging devices may gather pixel mapping data or values from the entire growth plate or any of the subsections shown and described herein.

In yet other embodiments, several imaging devices may be positioned throughout the reader for generating any of the images show and described herein at a variety of angles with respect to the growth plates. For instance, in some examples the reader may include at least a top and a bottom imaging device, while in other examples the reader may include one mobile imaging device that is capable of moving around, or within, the reader to capture images/scans from the top and bottom perspectives of the growth plates.

In use, the plate imaging unit may be a dynamic tool for monitoring biological agents and development on growth plates, or similar mediums. Generally, the reader system includes imaging technology for observing and quantifying biological growth, when present. In this way, Applicants have unexpectedly discovered the systems shown and described herein enhance the ability to observe changes in the plate development earlier than provided for in conventional systems. Further, the systems and methods herein predict a final result before the final result is actually visible by the human eye. For instance, the systems and methods herein are more sensitive than the human eye and conventional assemblies. In addition, the systems and methods herein monitor the growth plate to find variability prior to test development. For instance, the systems and methods herein establish a more accurate baseline for measuring changes in the growth plate than provided for in the conventional assemblies.

In use, the preliminary image may be first captured with any of the imaging devices shown and described herein under an install calibration. In one example, the settings that configure any optical system for ideal image capture may be predefined during the calibration phase of system installation. Periodic recalibration may be required due to system aging and metrological conditions. Calibration is achieved with pre-printed sample plates. For instance, optimization of lighting intensity, camera focus and camera exposure time may be defined at calibration time.

In one example, mechanical alignment of the growth plate 20 is achieved by drawing a digital circle around the sample area. This digital circle may be manipulated via keyboard, keystrokes to align the circumference and diameter with the sample plate area of interest. Typically, lighting intensity, exposure time, camera focus and mechanical alignment are configuration settings that remain constant after installation as shown and described herein.

As shown and described herein, the image area may be reduced to include only the area of interest that is predefined by the install calibration. Applicants have unexpectantly discovered this reduces processing time, in particular by not having to parse through uninteresting elements as understood by those skilled in the art having the benefit of this disclosure.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

What is claimed is:

1. A method for monitoring microbial colonies, when present, on a growth plate, said method comprising:
   a. receiving at least one growth plate having a recessed well, a pair of opposing proximate extensions, and a distal raised platform in a support frame, wherein said support frame having at least one proximate extension aperture and a distal platform aperture adapted to receive said growth plate parallel or below a horizontal upper plane of said support frame;
   b. selecting a non-automated plate type input chosen from at least a first plate type selection and a second plate type selection;
   c. imaging said growth plate with an imaging device aligned with said tray holder to generate an image;
   d. counting microbial colonies on said image; and
   e. identifying at least one alert count, when present, from comparing a background value identified on said growth plate to a non-background value identified on said growth plate, and comprising:
      i. pre-filtering said image,
      ii. thresholding said image, and
      iii. performing a histogram analysis of said image.

2. The method of claim 1, including generating a region of interest on said image.

3. The method of claim 1, including despeckling said image.

4. The method of claim 3, wherein despeckling said image includes performing an adjusted binary histogram.

5. The method of claim 1, including triggering an alert message.

6. The method of claim 5, including triggering a too numerous to count (TNTC) interpretation.

7. The method of claim 6, including overriding said suggested interpretation by identifying at least one spreader colony.

8. The method of claim 7, wherein said overriding includes identifying a plurality of large size particulates and grouping said particulates as a spreader colony.

9. The method of claim 6, including alerting a user to perform a manual determination.

10. The method of claim 1, including generating a percent ratio of colony-to-matrix output.

11. A method for monitoring imaging of microbial colonies on a growth plate, said method comprising:
    a. imaging said growth plate with an imaging device positioned above said growth plate being aligned parallel or below a horizontal upper plane in a support frame to generate at least one image;
    b. selecting a non-automated plate type input chosen from at least a first plate type selection and a second plate type selection;
    c. counting biological growth of microbial colonies, when present, on said image; and
    d. identifying alert counts on said image by comparing a background brightness value identified on said growth plate to a non-background brightness value identified on said growth plate.

12. The method of claim 11, including triggering a too numerous to count (TNTC) interpretation alert message.

13. The method of claim 12, including overriding said alert message when identifying a plurality of large size particulates and grouping said particulates as a spreader colony.

14. The method of claim 11, including generating a region of interest on said image.

15. The method of claim 11, including thresholding said image.

16. The method of claim 11, including performing a histogram analysis of said image.

17. The method of claim 16, including determining a percentage of said image corresponding with a blank image.

18. The method of claim 11, wherein said background and object non-background values comprise object size.

19. The method of claim 11, wherein said background and non-background values comprise brightness.

20. A method for monitoring a growth plate, said method comprising:
    a. receiving at least one growth plate in a support frame;
    b. selecting a non-automated plate type input chosen from at least a first plate type selection and a second plate type selection;
    c. imaging said growth plate with an imaging device aligned with said tray holder to generate an image;
    d. counting objects identified on said image; and
    e. identifying at least one alert count, when present, from comparing a background value identified on said growth plate to a non-background value identified on said growth plate.

* * * * *